US008343913B1

(12) United States Patent
Cowen et al.

(10) Patent No.: US 8,343,913 B1
(45) Date of Patent: Jan. 1, 2013

(54) HSP90, BUFFERING AND DRUG RESISTANCE

(75) Inventors: Leah Cowen, Jamaica Plain, MA (US); Susan L. Lindquist, Chestnut Hill, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 1442 days.

(21) Appl. No.: 11/175,515

(22) Filed: Jul. 5, 2005

Related U.S. Application Data

(60) Provisional application No. 60/693,188, filed on Jun. 22, 2005, provisional application No. 60/608,848, filed on Sep. 10, 2004, provisional application No. 60/585,038, filed on Jul. 2, 2004.

(51) Int. Cl.
| | |
|---|---|
| *A01N 37/18* | (2006.01) |
| *A01N 43/64* | (2006.01) |
| *A61K 38/00* | (2006.01) |
| *A61K 31/41* | (2006.01) |
| *A61K 45/00* | (2006.01) |
| *A61K 47/44* | (2006.01) |
| *A61P 31/10* | (2006.01) |
| *C07D 293/00* | (2006.01) |
| *C07D 421/00* | (2006.01) |
| *C07D 517/00* | (2006.01) |
| *C07D 291/00* | (2006.01) |
| *C07D 419/00* | (2006.01) |
| *C07D 515/00* | (2006.01) |
| *C07D 285/00* | (2006.01) |
| *C07D 417/00* | (2006.01) |
| *C07D 513/00* | (2006.01) |
| *C07D 273/00* | (2006.01) |
| *C07D 413/00* | (2006.01) |
| *C07D 498/00* | (2006.01) |
| *C07D 277/04* | (2006.01) |
| *C07D 277/08* | (2006.01) |
| *C07D 275/02* | (2006.01) |
| *C07D 249/08* | (2006.01) |
| *C07D 233/00* | (2006.01) |
| *C07D 233/02* | (2006.01) |
| *C07D 231/00* | (2006.01) |

(52) U.S. Cl. ...... 514/3.3; 514/359; 424/283.1; 548/100; 548/122; 548/123; 548/124; 548/146; 548/206; 548/240; 548/262.2; 548/300.1; 548/356.1

(58) Field of Classification Search .................. 514/171, 514/3.3, 359; 424/283.1; 548/100, 122, 548/123, 124, 146, 206, 240, 262.2, 300.1, 548/356.1
See application file for complete search history.

(56) References Cited

OTHER PUBLICATIONS

Burnie, J and Matthews, R. Expert Opin. Biol. Ther. (2004) 4 233-241.*

Burnie et. al., Expert Opinion Biol. Ther., 2004, Ashley Publications, vol. 4, issue 2, pp. 233-241.*
Matthews et. al., Antimicrobial Agents & Chemotherapy, 2003, American Society for Microbiology, vol. 47, No. 7, pp. 2208-2216.*
Soga et. al., Current Cancer Drug Targets, 2003, Bentham Science Publishers, vol. 3, pp. 359-369.*
Matthews et. al., Vaccine, 2004, Elsevier, vol. 22, pp. 865-871.*
Anderson, et al., "Haploidy, Diploidy and Evolution of Antifungal Drug Resistance in *Saccharomyces cerevisiae,*" *Genetics*, 168:1915-1923 (2004).
Anderson, et al., "Mode of Selection and Experimental Evolution of Antifungal Drug Resistance in *Saccharomyces cerevisiae,*" *Genetics*, 163:1287-1298 (2003).
Bagatell and Whitesell, "Altered Hsp90 function in cancer: A unique therapeutic opportunity," *Molecular Cancer Therapeutics*, 3(8):1021-1030 (2004).
Blankenship, et al., "Teaching old drugs new tricks: Reincarnating immunosuppressants as antifungal drugs," *Current Opinion in Investigational Drugs*, 4(2):192-199 (2003).
Borkovich, et al., "Hsp82 is an Essential Protein That Is Required in Higher Concentrations for Growth of Cells at Higher Temperatures," *Molecular and Cellular Biology*, 9(9):3919-3930 (1989).
Chang and Lindquist, "Conservation of Hsp90 Macromolecular Complexes in *Saccharomyces cerevisiae,*" *The Journal of Biological Chemistry*, 269(40):24983-24988 (1994).
Chang, et al., "In Vivo Analysis of the Hsp90 Cochaperone Sti1 (p60)," *Molecular and Cellular Biology*, 17(1):318-325 (1997).
Cowen, et al., "Evolution of Drug Resistance in *Candida albicans,*" *Annu. Rev. Microbiol.*, 56:139-165 (2002).
Hemenway and Heitman, "Calcineurin. Structure, Function and Inhibition," *Cell Biochemistry and Biophysics*, 30:115-151 (1999).
Imai and Yahara, "Role of HSP90 in Salt Stress Tolerance via Stabilization and Regulation of Calcineurin," *Molecular and Cellular Biology*, 20(24):9262-9270 (2000).
Kamal, et al., "Therapeutic and diagnostic implications of Hsp90 activation," *TRENDS in Molecular Medicine*, 10(6):283-290 (2004).
Kontoyiannis, et al., "Combination of caspofungin with inhibitors of the calcineurin pathway attenuates growth in vitro in *Aspergillus* species," *Journal of Antimicrobial Chemotherapy*, 51:313-316 (2003).
Lindquist. Stress Protein Plays a Role in the Evolution of Drug Resistance in Fungi. Division of Extramural Research and Training [online], [retrieved on Apr. 16, 2007]. Retrieved from the internet <URL: http://www.niehs.nih.gov/dert/profiles/hilites/2005/resist.htm>.
Nathan, et al., "In vivo functions of the *Saccharomyces cerevisiae* Hsp90 chaperone," *Proc. Natl. Acad. Sci. USA*, 94:12949-12956 (1997).
Odds, et al., "Antifungal agents: mechanisms of action," *TRENDS in Microbiology*, 11(6):272-279 (2003).
Picard, "Heat-shock protein 90, a chaperone for folding and regulation," *Cellular and Molecular Life Sciences*, 59:1640-1648 (2002).
Queitsch, et al., "Hsp90 as a capacitor of phenotypic variation," *Nature*, 417:618-624 (2002).
Roe, et al., "Structural Basis for Inhibition of the Hsp90 Molecular Chaperone by the Antitumor Antibiotics Radicicol and Geldanamycin," *Journal of Medicinal Chemistry*, 42:260-266 (1999).

(Continued)

*Primary Examiner* — Sreeni Padmanabhan
*Assistant Examiner* — Sarah Pihonak
(74) *Attorney, Agent, or Firm* — Ropes & Gray LLP

(57) ABSTRACT

A method of reducing antifungal drug resistance in which Hsp inhibitors, such as Hsp90 inhibitors, are used.

27 Claims, 8 Drawing Sheets

OTHER PUBLICATIONS

Rutherford and Lindquist, "Hsp90 as a capacitor for morphological evolution," *Nature*, 396:336-342 (1998).

Sanglard, "Resistance of human fungal pathogens to antifungal drugs," *Current Opinion in Microbiology*, 5:379-385 (2002).

Sanglard, et al., "Calcineurin A of *Candida albicans*: involvement in antifungal tolerance, cell morphogenesis and virulence," *Molecular Mircobiology*, 48(4):959-976 (2003).

Sangster, et al., "Under cover: causes, effects and implications of Hsp90-mediated genetic capacitance," *BioEssays*, 26:348-362 (2004).

Steinbach, et al., "In Vitro Interactions between Antifungals and Immunosuppressants against *Aspergillus fumigatus*," *Antimicrobial Agents and Chemotherapy*, 48(5):1664-1669 (2004).

White, "Increased mRNA Levels of *ERG16, CDR, and MDR1* Correlate with Increases in Azole Resistance in *Candida albicans* Isolates from a Patient Infected with Human Immunodeficiency Virus," *Antimicrobial Agents and Chemotherapy*, 41(7):1482-1487 (1997).

Whitsell, et al., "Inhibition of heat shock protein HSP90-pp60$^{v-src}$ heteroprotein complex formation by benzoquinone ansamycins: Essential role for stress proteins in oncogenic transformation," *Proc. Natl. Acad. Sci. USA*, 91:8324-8328 (1994).

Xu, et al., "Maturation of the tyrosine kinase c-src as a kinase and as a substrate depends on the molecular chaperone Hsp90," *Proc. Natl. Acad. Sci. USA*, 96:109-114 (1999).

Young, et al., "Hsp90: a specialized but essential protein-folding tool," *The Journal of Cell Biology*, 154(2):267-273 (2001).

Zhao, et al., "Navigating the Chaperone Network: An Integrative Map of Physical and Genetic Interactions Mediated by the Hsp90 Chaperone," *Cell*, 120:715-727 (2005).

\* cited by examiner

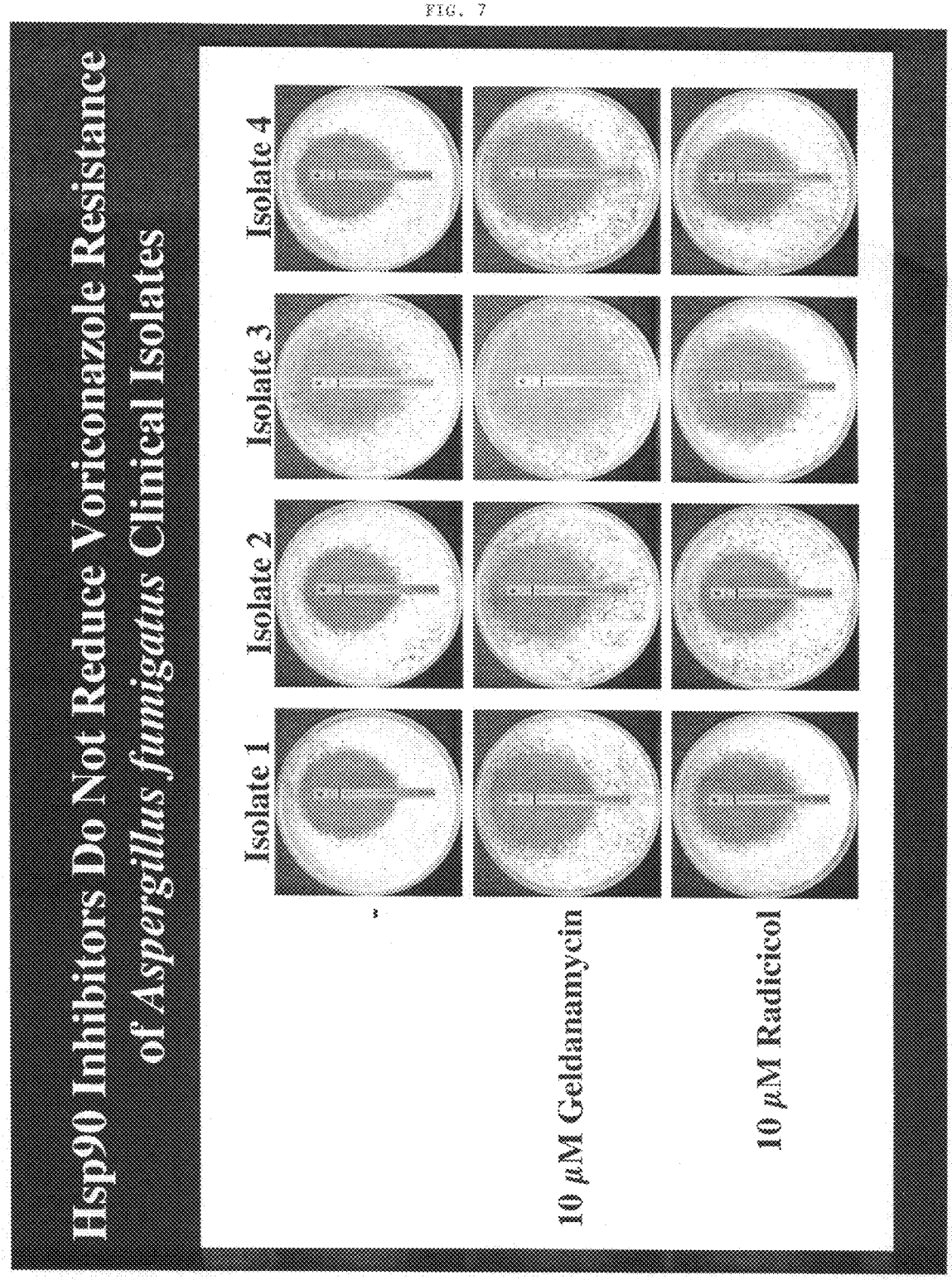

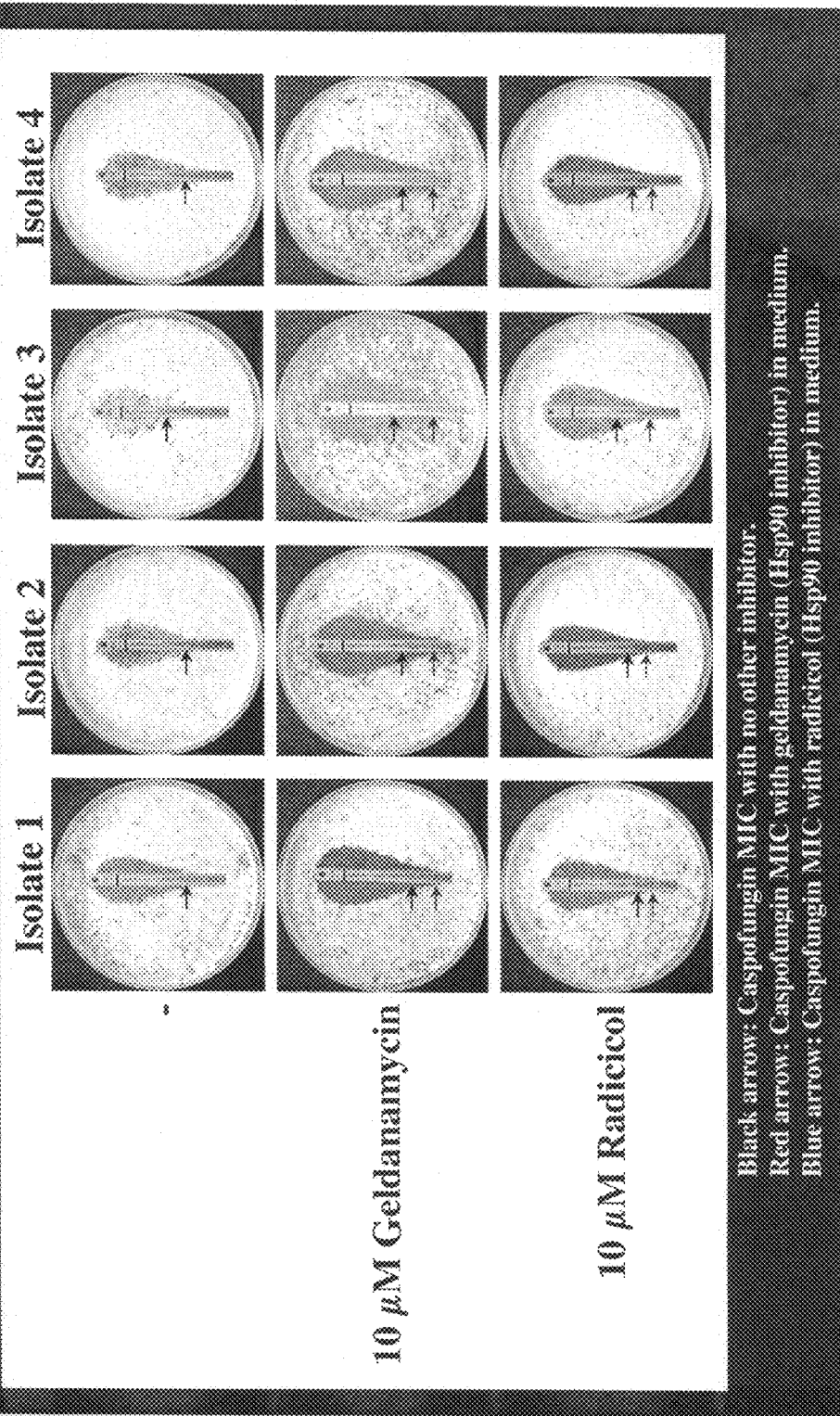

HSP90, BUFFERING AND DRUG RESISTANCE

RELATED APPLICATIONS

The present application claims the benefit of U.S. Provisional Application No. 60/585,038, filed Jul. 2, 2004, by Leah Cowen and Susan L. Lindquist, entitled "Hsp90, Buffering and Drug Resistance"; U.S. Provisional Application No. 60/608,848, filed Sep. 10, 2004, by Leah Cowen and Susan L. Lindquist, entitled "Hsp90, Buffering and Drug Resistance"; and U.S. Provisional Application No. 60/693,188, filed Jun. 22, 2005, by Leah Cowen and Susan L. Lindquist, entitled "Hsp90 Potentiates the Rapid Evolution of New Traits: Drug Resistance in Diverse Fungi." The referenced applications are incorporated herein in their entirety by reference.

FUNDING

Work described herein was funded, in whole or in part, by National Institute of Environmental Health Sciences Grant P30ES02109. The United States government has certain rights in the invention.

BACKGROUND OF THE INVENTION

Hsp90 is an essential molecular chaperone with a highly specialized function (1-3). Under physiological conditions, it regulates the folding, transport, maturation, and degradation of a diverse, but select set of client proteins, many of which are key regulators of cell signalling circuitry (4). Hsp90's clients include transcription factors and kinases that regulate processes as diverse as cell growth and division, development, apoptosis, immunity, and responses to hormones and other environmental signals (5). Details vary, but a common feature of many Hsp90 clients is a tendency to dwell in metastable, incompletely folded states. These proteins dynamically cycle through Hsp90 complexes until folding and activation are engendered by the binding of a ligand, insertion into a membrane, post-translational modification, or assembly with partner proteins.

An emergent property of Hsp90's function in chaperoning regulators of cell circuitry is a capacity to buffer the expression of genetic and epigenetic variation and release it in response to environmental stress (6-8). Under normal growth conditions, Hsp90 is expressed at much higher levels than are required for basal function. It is thereby intrinsically positioned to buffer variation. Protein folding, however, is exquisitely sensitive to diverse forms of environmental stress. Under such conditions, Hsp90 is induced, together with other heat shock proteins, to cope with this problem. Depending upon the genetic variation that has accumulated in particular genomes, however, the cellular demand for Hsp90 can exceed its level of induction. In the fly *Drosophila melanogaster*, the plant *Arabidopsis thaliana*, and likely in many other organisms, compromising Hsp90's buffering capacity by environmental stress, drugs, or mutations produces an extraordinary array of new phenotypes. While some of these phenotypes may be stochastic, others depend upon previously silent variation that can act in a combinatorial manner to produce new traits (6, 7). Importantly, after several generations of selection, polymorphisms that had been cryptic in progenitor organisms can be enriched in their progeny to the point that the phenotypes they produce are stably expressed even in one absence of stress (6). Thus, Hsp90 may play an important role in evolution by serving as a capacitor for the storage and release of genetic variation.

SUMMARY OF THE INVENTION

Described herein are methods of reducing drug resistance of fungi (reducing fungal drug resistance), such as methods of reducing resistance of yeast to drugs, including antibiotics, such as, but not limited to, azoles (e.g., fluconazole, voriconazole) and echinocandins (e.g., caspofungin) Also described are methods of enhancing effectiveness of a drug, particularly an antibiotic, in treating fungal (e.g., yeast) infections in mammals, particularly humans, by reducing resistance of the fungus/fungi(yeast strain(s)) to the drug (e.g., antibiotic). In the methods, resistance to an antibiotic is reduced (partially or completely) by reducing the function of an appropriate fungal (e.g., yeast) heat shock protein(Hsp) in the fungus (e.g., yeast), with the result that resistance to the antibiotic is reduced. In specific embodiments, Hsp90 function is inhibited, either directly (e.g., by preventing production or expression of Hsp90) or indirectly (e.g., by blocking the activity or availability of Hsp90). As a result, fungal drug resistance is reduced; in specific embodiments, resistance of yeast, such as *S. cerevisiae, Candida albicans* and other *Candida* strains, *Aspergillus fumigatis, terreus* and other *Aspergillus* strains, is reduced. The amount of antibiotic and/or the duration of treatment can be reduced as a result. In one embodiment, an individual, such as a human or other mammal who is being treated for a suspected or confirmed fungal infection, such as a yeast infection, is given an antifungal drug, such as an azole or an echinocandin, as well as an Hsp inhibitor, such as an Hsp90 inhibitor (e.g., geldanamycin or an analogue thereof; radicicol). This is referred to herein as coadministration. When they are coadministered, the two may be given simultaneously or sequentially and in either instance, may be given separately or in a single unit (which includes both the antifungal drug and the Hsp inhibitor). The Hsp inhibitor can be given prior to or after administration of the antifungal drug, provided that they are given sufficiently close in time that the Hsp inhibitor can have the desired effect of reducing (partially or totally) fungal resistance to the drug(s). One or more Hsp inhibitors and one or more antifungal drugs can be administered according to the present method. The antifungal drug(s) and Hsp inhibitor(s) can be given by a variety of routes, such as orally, intramuscularly, intraperitoneally, rectally, transdermally, intravenously or other appropriate route.

In particular embodiments, the present invention relates to a method of reducing antifungal drug resistance in an individual in need thereof, comprising coadministering to the individual at least one antifungal drug and at least one Hsp inhibitor. An individual in need thereof can be an individual in need of treatment with an antifungal drug, such as, for example, for a yeast infection. In specific embodiments, the individual in need thereof has a *Candida* infection or an *Aspergillus* infection. In the method, the antifungal drug can be any drug against which an individual might develop resistance that can be reduced (totally or partially) by means of inhibition of Hsp function, particularly Hsp90 function. For example, the at least one antifungal drug can be an azole or an echinocandin. The at least one Hsp90 inhibitor can be geldanamycin or an analogue thereof or radicicol. In certain embodiments, the individual in need thereof has an *Aspergillus fumigatus* infection and the at least one antifungal drug is caspofungin.

The present invention also relates to a method of enhancing the therapeutic effectiveness of an antifungal drug in an individual in need thereof, wherein the individual has or is likely to develop a drug resistant fungal infection, comprising coadministering to the individual at least one antifungal drug and at least one Hsp90 inhibitor. The drug resistant fungal infection can be, for example, a drug resistant yeast infection, such as a drug resistant *Candida* infection or a drug resistant *Aspergillus* infection. The at least one antifungal drug can be an azole or an echinochandin. The at least one Hsp90 inhibitor can be geldanamycin or an analogue thereof or radicicol. The individual in need thereof can have, for example, an *Aspergillus fumigatus* infection and the at least one antifungal drug can be caspofungin.

The present invention also relates to a method of inhibiting the development of antifungal drug resistance in an individual in need thereof, comprising coadministering to the individual at least one antifungal drug and at least one Hsp90 inhibitor. The individual in need thereof can have, for example, a *Candida* infection or an *Aspergillus* infection. The at least one antifungal drug can be an azole or an echinocandin. The, least one Hsp90 inhibitor can be geldanamycin or an analogue thereof or radicicol. The individual in need thereof can have an *Aspergillus fumigatus* infection and the at least one antifungal drug can be caspofungin.

In a further embodiment, the present invention is a pharmaceutical composition comprising at least one antifungal agent and at least one Hsp90 inhibitor. The antifungal agent(s) and Hsp90 inhibitor(s) can be any combination of those described herein or others result in the desired effect (enhanced availability of the antifungal agent(s), reduced antifungal resistance) in individuals to whom they are administered.

BRIEF DESCRIPTION OF THE DRAWINGS

FIG. 7. Hsp90 inhibitors do not reduce voriconazole resistance of *A. fumigatus* clinical isolates.

FIG. 8. Hsp90 inhibitors reduce caspofungin resistance of *A. fumigatus* clinical isolates.

SUPPLEMENTAL FIGURES

Figure 1:
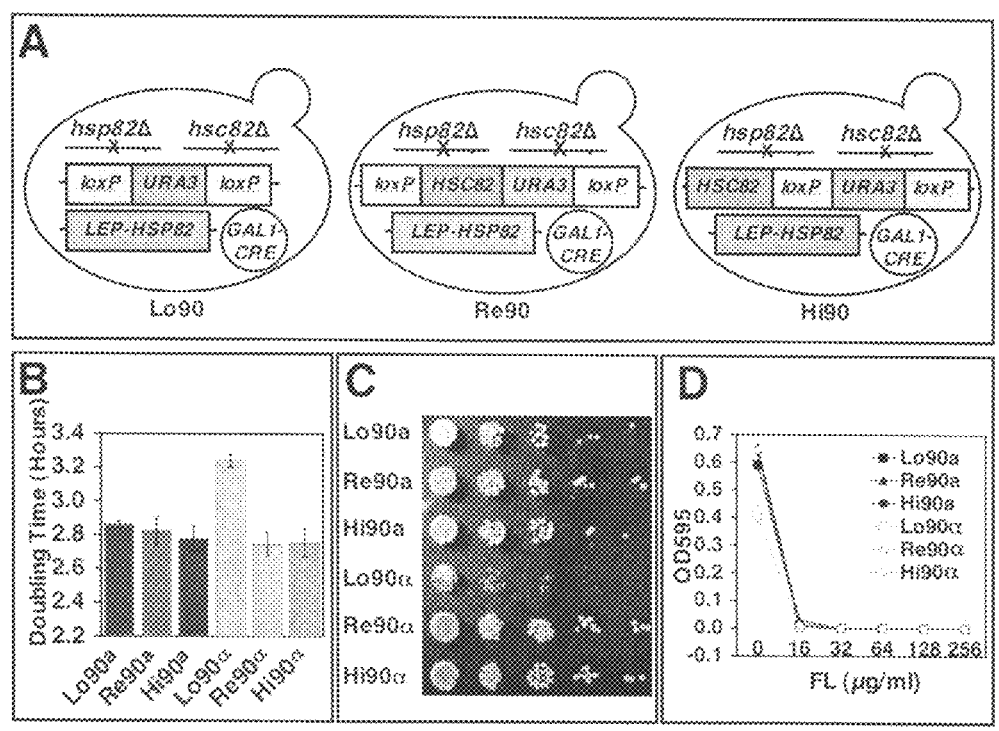
FIG. 1. Hsp90 enables rapid acquisition of fluconazole (FL) resistance and is required for its maintenance. (A) FL resistant colonies were recovered only in strains with high levels of Hsp90. For each strain, a photograph of part of one selection plate (128 µg/ml) is shown on top (red color develops in larger colonies in this strain). Images analyzed by CellProfiler are shown on bottom [see (18)]. Small abortive colonies (<0.67 mm$^2$) are in blue on the bottom image, intermediate colonies with moderate tolerance but no true resistance are in red, and larger colonies (>1.59 mm$^2$) with robust resistance to FL are in yellow. (B) Large colonies (FLR strains) showed strong resistance in rich medium at 23° C. The optical density (OD) of each well in minimum inhibitory concentration (MIC) test plates was averaged for duplicate measurements and normalized relative to FL-free control (see color bar). (C) Reducing Hsp90 expression by cre-mediated recombination eliminated FL resistance. FL resistance of large colonies in rich medium at 23° C. after cre-mediated recombination. Western blot analysis of Hsp90 levels relative to a tubulin loading control is shown below.

FIGS. S1A-S1D. Strains with Hsp90 expression levels under genetic control.
(A) In strain Lo90, a low expression HSP82 allele with a non-inducible promoter (LEP-HSP82) was the only source of Hsp90; cre-mediated recombination removed only a loxP-flanked URA3 marker. In strain Re90, a wild-type HSC82 allele was adjacent to the URA3 marker; cre-mediated recombination removed both HSC82 and URA3. In strain Hi90, the HSC82 allele was outside the loxP sequences; Cre-mediated recombination excised only the URA3 marker. (B) All strains of the MATa mating type grew equally well, but L90 strains of the MATα mating type grew less well. Doubling times in synthetic defined (SD) medium at 23° C. Growth of four replicates for each strain was monitored spectrophotomerically (Bioscreen C, Thermo Labsystems). Error bars are standard deviations. The reduced growth rate of Lo90 of the MATα mating type was observed in multiple independent Lo90α strains and was maintained over three rounds of back crossing to the parental strain. (C) Serial dilutions of cells spotted on SD medium and photographed after three days at 23° C. (D) All strains showed the same sensitivity to FL in SD medium at 23° C. Optical density (OD) of each well in minimum inhibitory concentration (MIC) test plates was determined spectrophotometrically for three replicates; error bars are standard deviations.

FIG. S2. Pdr1-mediated fluconazole (FL) resistance is robust to genetic reduction of Hsp90 expression.

Strains that had low levels of constitutive Hsp90 expression and had a wild-type PDR1 allele (Lo90-NL) were crossed with strains that had wild-type levels of Hsp90 and had a mutant PDR1 T817K allele (G1). After tetrad dissection, haploid progeny with reduced Hsp90 levels were identified by PCR and confirmed by Western blot analysis. Segregation of PDR1 alleles was determined by sequencing. FL resistance of the parental strains and the progeny with low levels of constitutive Hsp90 expression was determined in SD at 23° C. OD of each well in MIC test plates was averaged for duplicate measurements and growth was normalized relative to FL-free control (see color bar). Two haploid progeny that had low levels of Hsp90 and had the wild-type PDR1 allele (L90PDR1-W) and ten progeny that had low levels of Hsp90 and had the mutant PDR1 allele (L90PDR1-m) are shown. Progeny inheriting the PDR1 mutation showed various levels of fluconazole resistance, as expected since a second mutation contributing to the resistance phenotype was segregating in the cross (4). Importantly, no haploid progeny with the PDR1 mutation lost fluconazole resistance when Hsp90 levels were reduced.

FIG. S3. All strains responded to a selection regime with low fluconazole (FL) concentration.

Growth of three replicate populations of each strain that was under selection with 16 μg/ml FL was monitored spectrophotometrically.

FIG. S4. Inhibition of calcineurin phenocopies inhibition of Hsp90; fluconazole (FL) resistance of diverse mutants is reduced.

FL resistance was determined in rich medium at 30° C. (left panel), with inhibition of Hsp90 by GdA (middle panel), or with inhibition of calcineurin by CsA (right panel). OD of each well in MIC test plates was averaged for duplicate measurements and growth was normalized relative to FL-free control (see color bar).

FIG. S5. Inhibition of Hsp90 by RAD does not impair growth.

Serial dilutions of CAI4 and CaERG3/erg3 were spotted on SD medium (upper panel) and medium supplemented with 1 μM RAD (bottom panel). Plates were photographed after two days at 30° C. in the dark.

DETAILED DESCRIPTION OF THE INVENTION

As described herein, Applicants assessed whether Hsp90 can facilitate the emergence of new traits in free-living organisms by supporting the altered phenotypes produced by new mutations. To do so they examined the evolution of fungal drug resistance, which provides many experimental advantages. Resistant mutations are rapidly acquired (12); their phenotypic consequences are easily assayed (13); and multiple molecular mechanisms of resistance are known (14, 15). Further, the evolution of drug resistance is an ancient and ubiquitous process in nature as microorganisms continuously evolve new mechanisms for out-competing their neighbors.

In addition to serving as an excellent model for evolution, fungal drug resistance is also of great economic and biomedical importance. Fungi take an enormous toll on agricultural productivity and are common, and increasingly lethal, human pathogens. The number of clinically useful fungal drug targets remains limited and resistance has emerged for all of the drugs currently deployed.

Applicants investigated resistance to two different classes of drugs, azoles and echinocandins. Azoles have been the most clinically useful class of antifungal drugs for decades (14, 16). They target a fungal cytochrome P450 enzyme, Erg 11, which is required for the biosynthesis of ergosterol, the predominant sterol of fungal membranes. Resistance arises through multiple mechanisms, including: increases in Erg 11 expression, point mutations in Erg 11 that reduce azole binding, increases in multidrug transporters, alterations in sterol biosynthesis, and changes in membrane composition (12, 14). Echinocandins are the first new class of antifungal drugs to reach the clinic in decades, and mechanisms of resistance are not yet well characterized. Importantly, they have an entirely different mechanism of action from the azoles: they inhibit synthesis of β-(1,3) glucan, an essential component of fungal cell walls (16). Applicants examined fungi separated by one billion years of evolution (17): *Saccharomyces cerevisiae*, *Candida albicans*, and *Aspergillus terreus*. By chaperoning calcineurin, a key regulator of diverse cellular response pathways, Hsp90 allowed cells to acquire and maintain diverse mutations that create an immediate ability to resist antifungal drugs. Results described herein establish an entirely new facet to the emerging role of Hsp90 in evolutionary processes.

Hsp90 Potentiates the Acquisition of Fluconazole Resistance in *S. cerevisiae* Assessment began with *S. cerevisiae*, the most genetically tractable eukaryotic model organism. The Cre-Lox system was used to construct strains in which the abundance of Hsp90 could be altered by inducible recombination (18). *S. cerevisiae* has two functionally redundant Hsp90 genes, one (HSC82) is expressed constitutively at high levels, the other (HSP82) is strongly induced by increased temperature (19). Applicants genetically engineered a set of control strains to have a fixed low level of Hsp90 (Lo90 strains) and another set to have a fixed high level of Hsp90 expression (Hi90 strains). In Lo90 and Hi90 strains, cre-mediated recombination removes only a URA3 marker (FIG. S1A). Re90 strains were engineered to have a high constitutive level of Hsp90 expression that is reduced when cre-mediated recombination removes a cassette with HSC82 and the URA3 marker (FIG. S1A).

Consistent with the fact that *S. cerevisiae* generally expresses far more Hsp90 than is required for normal growth (19, 20), all strains of the MATa mating type grew equally well at 23° C. (FIGS. S1B and S1C). Lo90 strains of the MATα mating type grew less well, presumably because a pathway specific to the MATα cell-type requires high levels of Hsp90 for optimal fitness (FIG. S1B and S1C). This difference in growth rates did not affect the outcome of any of the experiments, ruling out the possibility that some general effect of Hsp90 on growth rates profoundly affected the evolution of drug resistance.

All strains exhibited the same sensitivity to the most commonly used azole fluconazole, with growth completely arrested at 16 μg/ml (S1D). A rapid, one-step selection regime, in which large numbers of cells were plated onto medium containing a high concentration of fluconazole (128 μg/ml), was used to select fluconazole-resistant mutants. Because fluconazole is fungistatic rather than fungicidal, under these conditions cells undergo an average of seven to nine doublings before fluconazole arrests growth (13). This produces many tiny, abortive colonies (FIG. 1A). Many intermediate sized colonies were also recovered. Upon further testing, these showed some tolerance to fluconazole, but they did not have true resistance [see (18)]. Only colonies of the largest size had acquired robust reproducible resistance.

Mating type did not affect the number of large colonies obtained (Fischer's Exact Test, $P \geq 0.2$), but Hsp90 levels had a highly significant impact ($P<5\times10^{-85}$). 115 large colonies were obtained from Hi90 and Re90, the strains with high levels of Hsp90. All twenty-four that were further tested had strong fluconazole resistance, with vigorous growth, even at 256 µg/ml (FIG. 1B and (21)). In contrast, only three large colonies were obtained from Lo90, and none showed true resistance upon further testing (18). Thus, the emergence of fluconazole resistance in response to this rapid, one-step selection regime depended upon high levels of Hsp90.

Hsp90 Plays a Crucial Role in these Resistant Phenotypes

Next Applicants asked if Hsp90 was required only to cope with the stress of the initial selection conditions or was intimately involved in enabling resistant phenotypes. To do so, cre recombinase was induced in twelve of the fluconazole-resistant mutants that were obtained by the rapid selection regime. Excision of the URA3 marker alone in Hi90-FLR cells had no effect on drug resistance in rich medium (FIG. 1C). In contrast, in Re90-FLR strains of both mating types, cre-mediated reductions in Hsp90 expression abolished resistance (FIG. 1C). Applicants also examined resistance to voriconazole, a newer azole with a broader activity spectrum. All FLR strains were resistant to voriconazole and this resistance was abrogated when Hsp90 expression was reduced (21). Thus, high levels of Hsp90 are required for azole resistance acquired by rapid selection.

The Role of Hsp90 in Fluconazole Resistance Depends on the Mode of Selection

Figure 2:
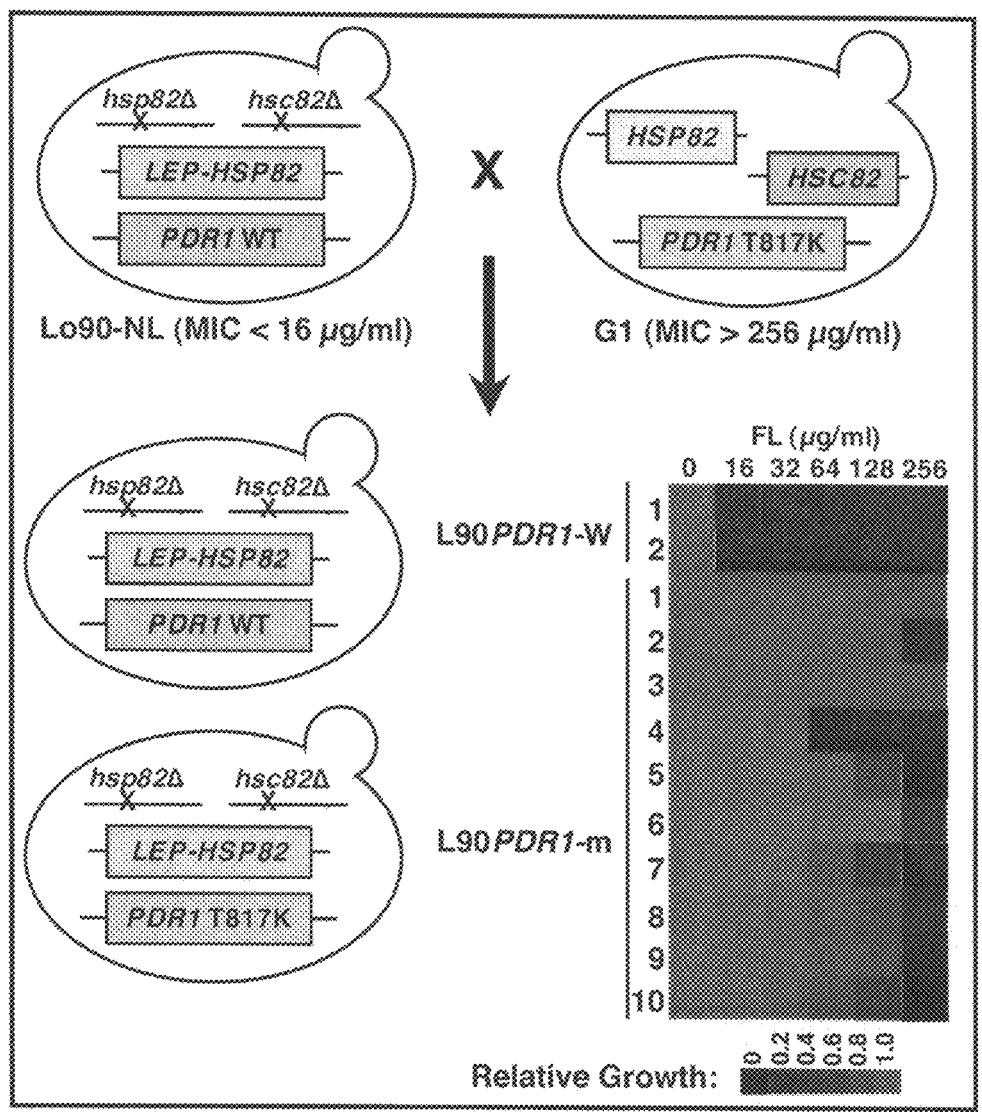
FIG. 2. Hsp90 is required for FL resistance acquired by rapid selection but not by gradual selection. Hsp90 was inhibited with geldanamycin (GdA, 5 µM) or radicicol (RAD, 5 µM) in FL MIC plates with SD medium at 30° C. (A) progenitor strains; (B) mutants obtained by rapid selection; and (C) mutants obtained by gradual selection. OD of each well in MIC test plates was averaged for three replicates and error bars are standard deviations. (D) High temperatures phenocopied the effects of Hsp90 inhibitors on FL resistance. Serial dilutions of cells were spotted on SD medium with 32 µg/ml FL (upper panels) and without FL (bottom panels) and photographed after two days.

S. cerevisiae is known to acquire high levels of azole resistance either when cells are suddenly exposed to a single high drug concentration (as above) or when cells are exposed to gradually increasing concentrations of fluconazole over 400 generations (13). Notably, the two modes of selection favor distinct mechanisms of resistance. To determine if Hsp90 plays a role in both, we employed six strains isolated in another laboratory, three by rapid selection (R1-3) and three by gradual selection (G1-3) (13). In this case, we employed pharmacological inhibition of Hsp90. Geldanamycin (GdA) and radicicol (RAD) are structurally unrelated, potent Hsp90 inhibitors that bind with high affinity to Hsp90's unusual ATP binding pocket (22, 23). Applicants employed concentrations of GdA and RAD that: 1) did not impair growth on their own (FIG. 2, data points for 0 µg/ml fluconazole); 2) had no effect on the fluconazole sensitivities of the progenitor strains (FIG. 2A); and 3) importantly, phenocopied the effects of genetically reducing Hsp90 in the FLR strains discussed above (21). Both GdA and RAD abolished fluconazole resistance in R1-3 strains that had acquired it through rapid selection (FIG. 2B). In contrast, neither GdA nor RAD altered resistance in the G1-3 strains that had acquired it by gradual selection (FIG. 2C). Thus, Hsp90 is required to maintain the resistance acquired by rapid selection but not resistance acquired by gradual selection.

Drugs and genetic manipulations provide the most direct methods for assessing the contribution of Hsp90 to drug resistance. In nature, however, it is environmental stress that causes the global problems of protein misfolding that overwhelm Hsp90's function (24). Accordingly, Applicants compared the effects of heat stress on fluconazole resistance in strains obtained by rapid and gradual selection. Strains obtained by rapid selection showed a dramatic reduction in resistance at 39° C., while those obtained by gradual selection maintained it (FIG. 2D). These results were not simply due to a general effect of temperature on the growth of R1-3 strains; in the absence of fluconazole, all strains grew equally well. Thus, environmental stress recapitulates the effects of impaired Hsp90 function, with phenotypic consequences that are contingent on the underlying mechanism of resistance.

The Molecular Mechanism of Hsp90-Independent Resistance

The G1-3 strains examined above are known to have acquired resistance through mutations in the transcription factor Pdr1 that increase the expression of multidrug transporters (13). Thus, a trivial explanation for the robustness of fluconazole resistance of Pdr1 mutants to GdA and RAD is that the Hsp90 inhibitors are simply being pumped out of the cell. To directly determine if this mechanism of resistance is robust to the impairment of Hsp90 function, G1 was crossed to a strain with genetic reduction in Hsp90 expression (FIG. S2). Resistance was maintained in all of the progeny with the Pdr1 mutation and reduced Hsp90 expression. Thus, Pdr1-mediated resistance does not require high levels of Hsp90 function.

Figure 3:
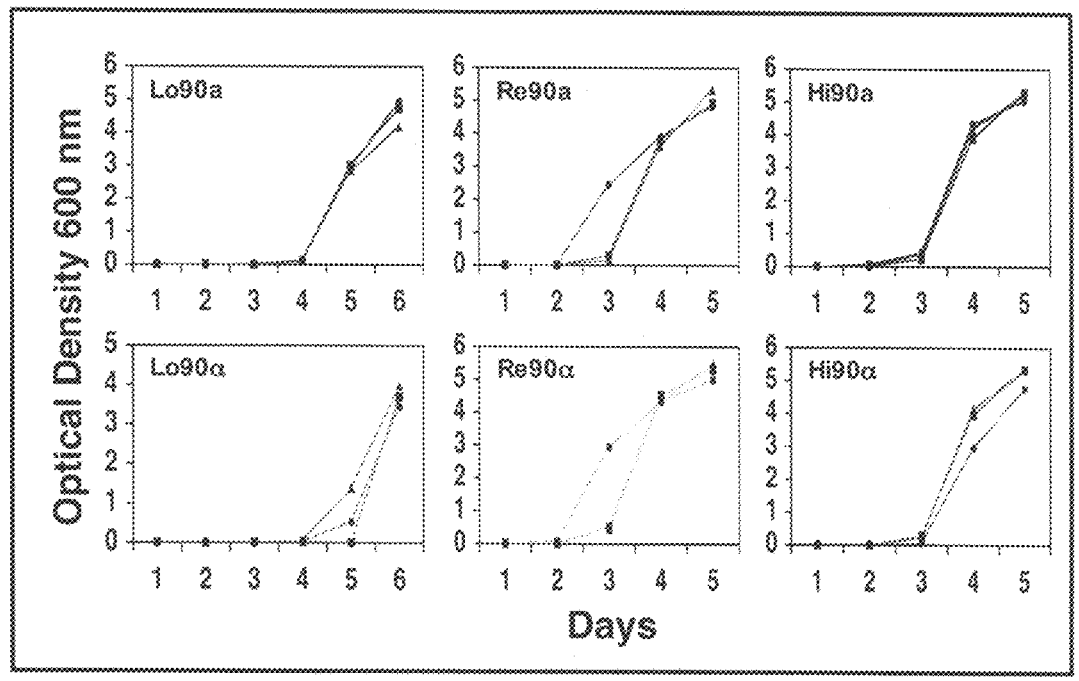
FIG. 3. Hsp90-independent fluconazole (FL) resistance involves the increased expression of a drug pump. Top, FL resistance of the progenitor strains (P) and mutants acquired by selection with 16 µg/ml FL (M1-3) in SD at 23° C. Data analyzed as in FIG. 1. Bottom, Western blot analysis of Pdr5 relative to tubulin loading control is shown below.

Given these observations, strains with reduced Hsp90 levels should be able to evolve fluconazole resistance when selected by a regime that favors Pdr1-based pathways. Applicants used a low drug concentration regime (16 µg/ml) that favors mutations in Pdr1 and the closely related transcription factor Pdr3 (25). Triplicate populations with low Hsp90 (Lo90) and high Hsp90 (Re90 and Hi90) remained static for several days of exposure to fluconazole and then initiated vigorous growth (FIG. S3). The cultures were plated to isolate individual colonies for further characterization. Each showed true resistance to fluconazole (FIG. 3). Moreover, each isolate overexpressed the multidrug transporter Pdr5, consistent with a mutation in Pdr1 or Pdr3 (FIG. 3). Thus, Pdr1-mediated resistance can both be acquired and maintained independently of Hsp90, in contrast to the crucial role of Hsp90 in resistance acquired by rapid, acute selection.

The Molecular Mechanisms of Hsp90-Dependent Resistance

Azoles block fungal growth by inhibiting Erg11, resulting in the accumulation of toxic intermediates in the ergosterol biosynthesis pathway (14). The rapid, one-step fluconazole selection regime favors mutations in Erg3 that block ergosterol synthesis at an earlier stage and prevent the accumulation of toxic intermediates (13). Erg3 mutants have altered membrane sterol composition but can grow in the presence of azoles (14). Indeed, twelve of the twelve ERG3 genes sequenced in strains obtained by rapid selection contained mutations, most of which introduced stop codons or frameshifts (table S1, Re90-FLR and Hi90-FLR).

To gain a more global view of the role of Hsp90 in potentiating the evolution of azole resistance, Applicants took advantage of a previous screen, in which ~4700 viable haploid S. cerevisiae deletion mutants were tested for enhanced fluconazole resistance (13). The thirteen deletion mutants that had increased resistance were enriched for genes involved in lipid, fatty acid, and sterol metabolism (13). They tested the impact of Hsp90 inhibition on fluconazole resistance of the eleven mutants available in their collection: erg3Δ, erg6Δ, ymr102cΔ, ymr099cΔ, ypl056cΔ, osh1Δ, scs2Δ, cka2Δ, ybr147wΔ, ygr283cΔ, and ylr407wΔ. GdA and RAD reduced the fluconazole resistance in all of them (FIG. 4A and FIG. S4). Clearly, Hsp90 modulates multiple genotype-to-phenotype relationships involved in the resistance to azoles.

The Relationship Between Hsp90-Mediated Drug Resistance and Calcineurin

Because calcineurin is an Hsp90 client protein that regulates numerous cellular responses to environmental stimuli, including the response to azoles (26, 27), Applicants hypothesized that Hsp90 affects fluconazole resistance via calcineurin. Calcineurin is a highly conserved $Ca^{2+}$/calmodulin activated protein phosphatase that regulates cell cycle progression, morphogenesis, and virulence in fungi (28). As with other client proteins, Hsp90 keeps calcineurin poised for activation and enables calcineurin-dependent responses (29). If Hsp90's effects on fluconazole resistance work through calcineurin, then inhibition of calcineurin should phenocopy inhibition of Hsp90.

Figure 4:
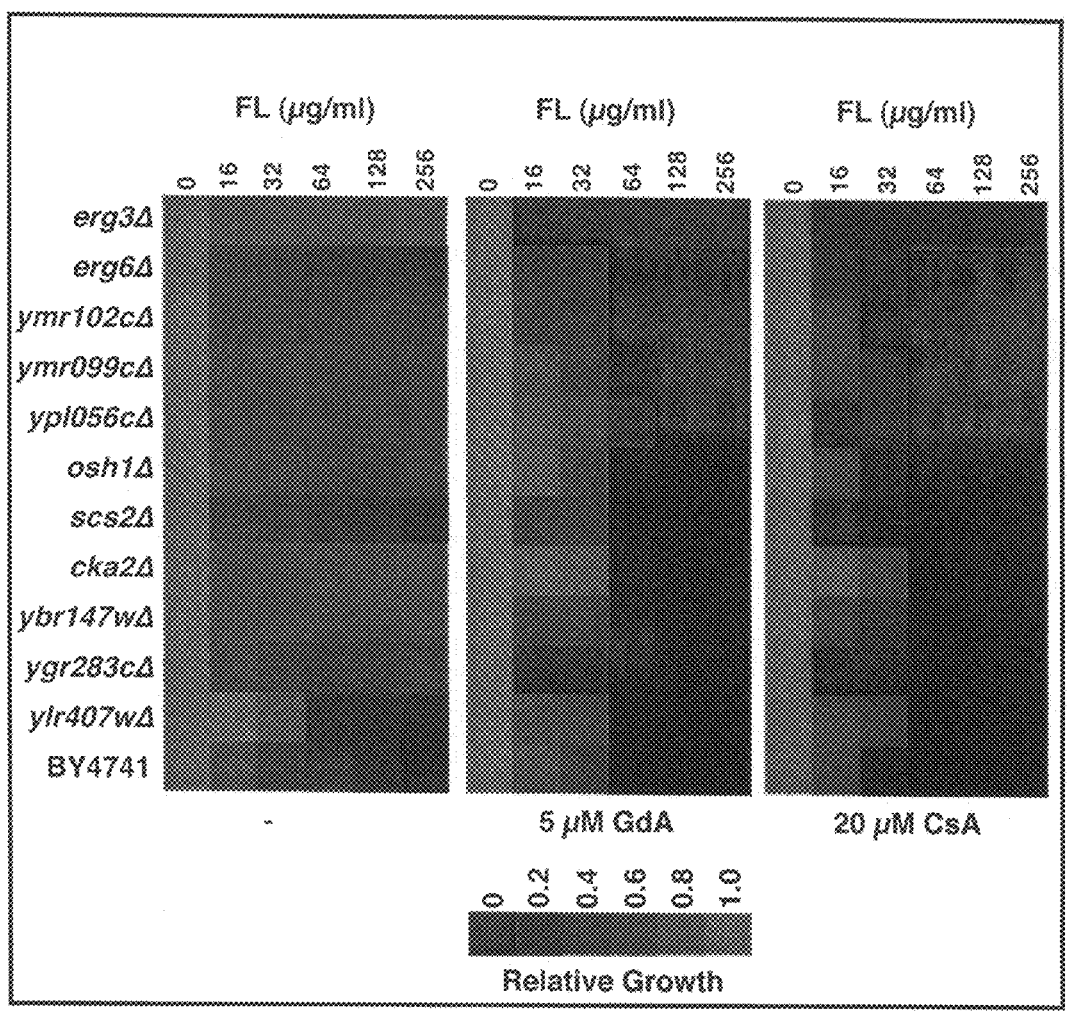
FIG. 4. Hsp90 and calcineurin are required for FL resistance acquired through diverse mutations. Approximately 4×10$^6$ cells/ml were spotted on rich medium with or without 64 µg/ml fluconazole (FL) and photographed after two days at 30° C. Top two panels, deletion mutants. Bottom panel, control strains obtained by rapid (R1-3) and gradual (G1-3) selection. (A) Hsp90 was inhibited by GdA (5 µM) or RAD (1 µM), as indicated. (B) Calcineurin was inhibited by cyclosporin A (CsA, 20 µM). Concordant results were obtained by MIC testing, which revealed that the magnitude of the inhibitors effects on resistance differed among the mutants (FIG. S4).

Cyclosporin A (CsA) is a well-known and potent calcineurin inhibitor (30). As with GdA and RAD, Applicants used a concentration of CsA that did not inhibit fungal growth on its own (FIG. 4B). Strikingly, CsA reduced fluconazole resistance or all or the mutants except Pdr1 mutants (strains G1-3), concordant with the effects of Hsp90 inhibition by GdA and RAD (FIG. 4). These results strongly suggest that Hsp90 potentiates the resistance of many different mutants through a common regulator, calcineurin. This conclusion was also confirmed through genetic analysis.

Hsp90 Potentiates the Evolution of Drug Resistance in *Candida Albicans*

The next question asked was whether Hsp90 potentiates the evolution of fluconazole resistance in *C. albicans*, an important human pathogen that is estimated to have diverged from a common ancestor with *S. cerevisiae* ~800 million years ago (17). In *S. cerevisiae*, the rapid selection regime favors recessive ERG3 mutations. Because *C. albicans* is diploid, both a standard lab strain (CAI4) and a heterozygous ERG3 deletion mutant (CaERG3/erg3) were used for the selection experiment. Both strains were sensitive to fluconazole, with growth completely arrested at 16 µg/ml (21). When large numbers of cells were plated on medium with 128 µg/ml fluconazole, many colonies were recovered (FIG. 5A). In contrast, when cells were plated on medium with fluconazole and RAD, no colonies were recovered. This was not due to a general deleterious effect of the Hsp90 inhibitor on growth, since RAD had no effect on growth in the absence of fluconazole (FIG. S5).

Surprisingly, the heterozygous ERG3 mutant did not produce more resistant mutants than the standard lab strain. This suggested that recessive ERG3 mutations were not the main route to drug resistance under this selection regime in *C. albicans*. Indeed, DNA sequence analysis revealed no ERG3 mutations in the six resistant colonies tested (three from each genotype). Thus, different molecular mechanisms are favored by this mode of selection in *C. albicans* and *S. cerevisiae* but the central role of Hsp90 in facilitating the rapid acquisition of resistance is conserved.

The Importance of Hsp90 in the Evolution of *C. Albicans* Drug Resistance in a Human Host To investigate the impact of Hsp90 on a natural evolutionary process, Applicants employed a series of *C. albicans* clinical isolates (CaCi) that had been collected from a single HIV-infected patient over the course of two years of treatment with fluconazole. Detailed genomic analysis indicated that these isolates represent a single strain that evolved increasing levels of resistance by multiple mechanisms (31). Examining resistance of these strains to fluconazole in two different media yielded complementary insights into the role of Hsp90 (FIGS. 5B and C).

In rich medium, all of the clinical isolates were more resistant to fluconazole than the standard lab strain (CAI4), with only subtle increases in resistance evident over the course of the in vivo selection (FIG. 5l3, left panel). Differences among the clinical isolates were more apparent in a defined medium that mimics the nutrient poor environment in the human host and is the standard for clinical testing (FIG. 5C, left panel). In both the defined medium (21) and even in rich medium (FIG. 5B), where levels of resistance were extremely high for all of the clinical isolates, inhibition of Hsp90 by GdA or calcineurin by CsA reduced resistance. Hsp90 inhibition affected isolates recovered early during treatment far more dramatically than those recovered later in treatment. Thus, under the natural forces that shaped pathogen evolution in this patient, Hsp90 was initially vital for the acquisition of resistance. However, as cells acquired additional mutations, driven by continued selective pressures, the trait evolved towards independence from high levels of Hsp90 function.

Next, Applicants asked if the effect of the Hsp90 inhibitor could be phenocopied by natural environmental stress. Specifically, they tested the effects of 39° C. or 41° C., temperatures that are reached in humans challenged by infections. In the medium most similar to conditions of the human host, thermal stress recapitulated the effects of Hsp90 inhibition (FIG. 5C). A similar effect was also seen in rich medium (21). Elevated temperatures strongly reduced drug resistance in the early isolates, and moderately reduced it in later isolates. Thus, results established a powerful connection between fluctuations in Hsp90-mediated phenotypes and environmental stress. Furthermore, the results suggest one molecular mechanism for a beneficial clinical effect of fever: the pathogen becomes susceptible to drug-induced changes in signaling networks and drug resistance is reduced.

Hsp90 Modulates Caspofungin Resistance in *Aspergillus Terreus*

To further broaden our understanding of Hsp90's role in drug resistance, Applicants turned to *Aspergillus*, a filamentous ascomycete that is estimated to have diverged from a common ancestor with *Candida* and *Saccharomyces* (hemiascomycetes) ~one billion years ago (17). While *A. fumigatus* is the more prevalent human pathogen, *A. terreus* is also clinically important (32), and the strain used can be handled without serious biosafety concerns. *Aspergillus* species are resistant to many antifungal drugs, posing an extreme therapeutic challenge. To provide a rapid, quantitative assessment of drug resistance Etest strips were used to create a gradient of drug concentration in solid medium.

Figure 6:
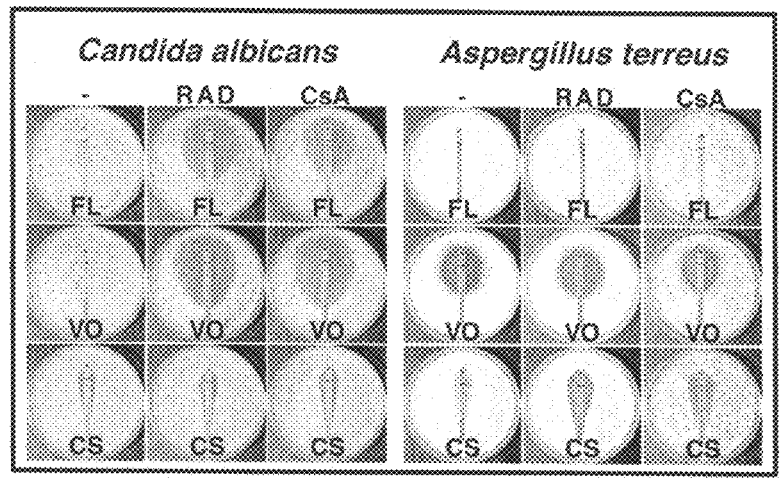
FIG. 6. Hsp90 potentiates resistance to different drugs in *C. albicans* and *A. terreus*. Resistance of *C. albicans* clinical isolate T118 and *A. terreus* soil isolate ATCC 10020 to the azoles, fluconazole (FL) and voriconazole (VO), and to the echinocandin, caspofungin (CS) on rich medium determined by Etest strips, which produce a gradient of drug concentrations, oriented with the highest concentration at the top [see (18)]. Plates contained the Hsp90 inhibitor RAD (5 µM) or the calcineurin inhibitor CsA (20 µM). The MIC value is where the inhibition ellipse intersects the strip.

Consistent with the broader efficacy spectrum of voriconazole, *A. terreus* was much more sensitive to this azole than to fluconazole. While Hsp90 and calcineurin inhibitors dramatically reduced the resistance of *C. albicans* to both fluconazole and voriconazole, they did not reduce the resistance of *A. terreus* to these azoles (FIG. 6). Hsp90 inhibitors did not reduce voriconazole resistance of *A. fumigatus* clinical isolates (FIG. 7). Next Applicants examined resistance to the echinocandins, which block cell wall synthesis and are the only new class of antifungals to reach the clinic in decades. Calcineurin inhibitors have recently been reported to increase the sensitivity of *Aspergillus* to the echinocandin casopofungin (33, 34), confirmed in FIG. 6. Results showed that an Hsp90 inhibitor had an equally strong effect. In contrast, inhibitors of calcineurin or Hsp90 did not alter the resistance of *C. albicans* to caspofungin. Hsp90 inhibitors reduced caspofungin resistance of *A. fumigatus* clinical isolates (FIG. 8). Thus, Hsp90 has profound but distinct effects on drug resistance in evolutionary distant fungal pathogens.

Discussion

Our results establish a new role for Hsp90 in the evolution of adaptive traits. In fungal species separated by ~one billion years of evolution, Hsp90 potentiates the emergence of drug resistance by enabling new mutations to have immediate phenotypic consequences. Resistance acquired by diverse mutations disappears when Hsp90 function is reduced. Importantly, Hsp90 normally plays little role in general stress tolerance (4). Its role in drug resistance is to enable crucial specific responses to particular stresses via calcineurin, itself a key sensor of environmental stress and regulator of cell signaling. In *Sachharomyces cerevisiae* and *Candida albicans* Hsp90 enables cells to cope with membrane perturbations caused by the azoles. In *Aspergillus terreus* it enables cells to cope with alterations in cell wall synthesis caused by an echinocandin. Because many mutations are expected to imbalance signaling and to stress particular cellular processes, this role of Hsp90 in the evolution of new traits may be much broader than in drug resistance alone.

Previous work in other organisms suggests that Hsp90 can affect the evolution of new traits in two very different ways. First, in *Arabidopsis* and *Drosophila*, Hsp90 allows the storage of cryptic genetic variation that can be revealed in a genome-wide, combinatorial fashion. In this case the new traits appear when Hsp90 buffering capacity is compromised (6, 7). Second, in mammalian cancer cells, Hsp90 allows diverse cell regulators to tolerate mutations that make them prone to misfolding and simultaneously activate their oncogenic potential (10, 22). By directly chaperoning the mutant regulators, Hsp90 enables malignant transformation. In this case, the new traits are lost when Hsp90 function is compromised. In the evolution of fungal drug resistance, new traits are also lost when Hsp90 function is compromised. Unlike its effects in cancer cells, Hsp90 does not directly enable the function of newly mutated proteins; it is the loss of their function (which can be equally achieved through deletion mutations) that enables resistance phenotypes. Hsp90 exerts its effects on resistance by chaperoning normal (unmutated) regulators of cell signaling, thereby creating new circuit properties that enable disparate loss-of-function mutations in the genome to create adaptive phenotypes. These different effects of Hsp90 were uncovered in experiments employing different model organisms. It is likely, however, that in many organisms Hsp90 can contribute to the evolution of new traits in all three ways.

Strikingly, traits emerging through very different Hsp90-mediated effects can evolve to have little dependence on Hsp90. In *Drosophila*, this occurred predominantly through the enrichment of pre-existing polymorphisms during continued rounds of mating and selection (6). In fungi, drug resistance evolved towards Hsp90 independence through the acquisition of new mutations. In the infected host, repeated episodes of fever may provide ideal selective conditions for the emergence of Hsp90 independence. In *C. albicans* isolated from a human host reduced dependence on Hsp90 corresponded with the upregulation of drug efflux pumps (31). For *S. cerevisiae* mutants, the overexpression of similar pumps bypassed the need for the specific cellular response pathways that were contingent upon high concentrations of Hsp90. Depending upon the organism, the trait and the environment, it may be advantageous for traits to retain a link to environmental stress, but it is clear that multiple mechanisms exist for them to lose environmental contingency.

Hsp90's role in the evolution of fungal drug resistance has broad therapeutic implications for managing life-threatening fungal infections. Strategies to improve the efficacy of existing antifungal drugs are critical due to the frequency with which resistance arises. Notably, calcineurin inhibitors have recently been recognized for their potential in antifungal therapy but their immunosuppressant effects may complicate their utility (35). Alternatively, Hsp90 inhibitors can be used. Drugs structurally related to GdA are currently in phase I/II clinical trials as anticancer agents (11, 36). With concentrations that are well tolerated by humans, Hsp90 inhibitors are at least as effective as calcineurin inhibitors in overcoming fungal drug resistance. Inhibiting Hsp90 may render fungal pathogens that are already recalcitrant to antifungal therapy more responsive to treatment and, when given in the initial stages of therapy, may impede the de novo evolution of drug resistance.

REFERENCES

1. J. C. Young, I. Moarefi, F. U. Hard, *J Cell Biol* 154, 267-73 (2001).
2. D. Picard, *Cell Mol Life Sci* 59, 1640-8 (2002).
3. W. B. Pratt, D. O. Toft, *Exp Biol Med (Maywood)* 228, 111-33 (2003).
4. D. F. Nathan, M. H. Vos, S. Lindquist, *Proc Natl Acad Sci USA* 94, 12949-56 (1997).
5. R. Zhao et al., *Cell* 120, 715-727 (2005).
6. S. L. Rutherford, S. Lindquist, *Nature* 396, 336-42 (1998).
7. C. Queitsch, T. A. Sangster, S. Lindquist, *Nature* 417, 618-24 (2002).
8. V. Sollars et al., *Nat Genet* 33, 70-4 (2003).
9. Y. Xu, S. Lindquist, *Proc Natl Acad Sci USA* 90, 7074-8 (1993).
10. Y. Xu, M. A. Singer, S. Lindquist, *Proc Natl Acad Sci USA* 96, 109-14 (1999).
11. R. Bagatell, L. Whitesell, *Mol Cancer Ther* 3, 1021-30 (2004).
12. L. E. Cowen, J. B. Anderson, L. M. Kohn, *Annu Rev Microbiol* 56, 139-65 (2002).
13. J. B. Anderson et al., *Genetics* 163, 1287-98 (2003).
14. D. Sanglard, *Curr Opin Microbiol* 5, 379-85 (2002).
15. T. C. White, K. A. Marr, R. A. Bowden, *Clin Microbiol Rev* 11, 382-402 (1998).
16. F. C. Odds, A. J. Brown, N. A. Gow, *Trends Microbiol* 11, 272-9 (2003).
17. D. S. Heckman et al., *Science* 293, 1129-33 (2001).
18. Materials and methods are available as supplemental material on Science Online.
19. K. A. Borkovich, F. W. Farrelly, D. B. Finkelstein, J. Taulien, S. Lindquist, *Mol Cell Biol* 9, 3919-30 (1989).
20. H. C. Chang, D. F. Nathan, S. Lindquist, *Mol Cell Biol* 17, 318-25 (1997).
21. L. E. Cowen, S. Lindquist, unpublished data.
22. L. Whitesell, E. G. Mimnaugh, B. De Costa, C. E. Myers, L. M. Neckers, Proc *Natl Acad Sci USA* 91, 8324-8 (1994).
23. S. M. Roe et al., *J Med Chem* 42, 260-6 (1999).
24. T. A. Sangster, S. Lindquist, C. Queitsch, *Bioessays* 26, 348-62 (2004).
25. J. B. Anderson, C. Sirjusingh, N. Ricker, *Genetics* 168, 1915-23 (2004).
26. M. C. Cruz et al., *Embo J* 21, 546-59 (2002).
27. D. Sanglard, F. Ischer, O. Marchetti, J. Entenza, J. Bille, *Mol Microbiol* 48, 959-76 (2003).
28. D. S. Fox, J. Heitman, *Bioessays* 24, 894-903 (2002).
29. J. Imai, I. Yahara, *Mol Cell Biol* 20, 9262-70 (2000).
30. C. S. Hemenway, J. Heitman, *Cell Biochem Biophys* 30, 115-51 (1999).
31. T. C. White, *Antimicrob Agents Chemother* 41, 1482-7 (1997).
32. M. A. Pfaller, D. J. Diekema, *J Clin Microbiol* 42, 4419-31 (2004).
33. D. P. Kontoyiannis, R. E. Lewis, N. Osherov, N. D. Albert, G. S. May, *J Antimicrob Chemother* 51, 313-6 (2003).
34. W. J. Steinbach et al., *Antimicrob Agents Chemother* 48, 1664-9 (2004).
35. J. R. Blankenship, W. J. Steinbach, J. R. Perfect, J. Heitman, *Curr Opin Investig Drugs* 4, 192-9 (2003).

36. A. Kamal, M. F. Boehm, F. J. Burrows, *Trends Mol Med* 10, 283-90 (2004).
37. J. D. Hasday, K. D. Fairchild, C. Shanholtz, *Microbes Infect* 2, 1891-904 (2000).
38. M. Kirschner, J. Gerhart, *Proc Natl Acad Sci USA* 95, 8420-7 (1998).
39. A. Bergman, M. L. Siegal, *Nature* 424, 549-52 (2003).
40. H. L. True, I. Berlin, S. L. Lindquist, *Nature* 431, 184-7 (2004).

Supporting Online Material
Materials and Methods
Plasmids

Recombinant DNA procedures were performed according to standard protocols (1). Primers used in this study are listed in table S2. Plasmids were sequenced to verify the absence of mutations. Plasmid pRS303-LEP-HSP82 is an integrating plasmid with an HSP82 allele that is expressed at low constitutive levels from a truncated promoter (2); it was constructed by PCR amplifying HSP82 from genomic DNA of strain W303 with primers HSP82-SpeI-F and HSP82-BamHI-R and cloning into pRS303 with SpeI and BamHI. Plasmid pUG72 contains a loxP flanked *Kluyveromyces lactis* URA3 marker (3). Plasmid pUG72-HSC82 in contains HSC82 and the URA3 marker within the loxP sequences; it was constructed by amplifying HSC82 with primers HSC82-SacI-F and HSC82-NcoIB-R from W303 and cloning into pUG72 with SacI and NcoI. Plasmid pUG72-HSC82out contains HSC82 outside the loxP sequences; it was constructed by amplifying HSC82 with primers HSC82-SacII-F and HSC82-SpeIB-R from W303 and cloning into pUG72 with SacII and SpeI. A set of integrating plasmids was constructed by cloning the loxP-flanked URA3 cassette from pUG72, the loxP-flanked HSC82 and URA3 cassette from pUG72-HSC82 in, and the cassette with HSC82 adjacent to the loxP-flanked URA3 marker of pUG72-HSC82out into pRS305 using SacII and PstI, generating plasmids pRS305-pUG72, pRS305-pUG72-HSC82 in, and pRS305-pUG72out respectively.

*Saccharomyces Cerevisiae* Strains

The complete list of *S. cerevisiae* strains used in this study is provided in table S1. Archives of all strains were maintained in 25% glycerol at $-80°$ C. Erg3 and Pdr1 mutants were obtained from selection experiments starting with a progenitor closely related to S288C (4). Strains from the yeast deletion collection each had a specific gene deletion generated with the KanMX4 (KAN) selectable marker in BY4741, a strain closely related to S288C (5, 6): erg3$\Delta$, erg6$\Delta$, ymr102c$\Delta$, ymr099c$\Delta$, ypl056c$\Delta$, osh1$\Delta$, scs2$\Delta$, cka2$\Delta$, ybr147w$\Delta$, ygr283c$\Delta$, ylr407w$\Delta$ (Invitrogen Corporation).

Strains that had fixed low levels of Hsp90 (Lo90), fixed high levels of Hsp90 (Hi90), or high levels of Hsp90 that could be reduced by cre-mediated recombination (Re90) were constructed in the W303 background (FIG. S1A). To minimize the number of sequential transformation steps, half of the genetic manipulations were done in one set of haploids and half were done in an isogenic set. For deletion of HSP82 in W303 strains of both mating types, the KAN cassette was amplified from plasmid pFA6a (7) with primers HSP82-KANMX4-F and HSP82-KANMX4-R. Standard transformation protocols were employed (7), followed by selection for the KAN marker on yeast peptone dextrose (YPD) plates (1) with 200 µg/ml geneticin (Gibco). Proper deletion was confirmed with two set of primers: 1) HSP82-1F and KANMX4-R and 2) HSP82-1R and KANMX4-F. Plasmid pRS303-LEP-HSP82 was linearized in HIS3 with NheI and integrated into the W303 haploids that had a deletion of HSP82. Proper genomic integration was confirmed with primers 5-pRS30X and HIS3-R. For deletion of HSC82 in separate W303 strains of both mating types, the KAN cassette was amplified from plasmid pFA6a with primers HSC82-KANMX4-F and HSC82-KANMX4-R. Proper deletion was confirmed with two sets of primers: 1) YMR185W-F and KANMX4-R and 2) YMR187C-R and KANMX4-F. Plasmids pRS305-pUG72, pRS305-pUG72-HSC82 in, and pRS305-pUG72out were linearized in LEU2 with BstXI for integration into the strains that had a deletion of HSC82. Proper genomic integration was confirmed with two sets of primers: 1) 5-pRS30X and LEU2-2R and 2) 3-PRS30X and LEU2-Down. Haploids that had HSP82 deleted and pRS303-LEP-HSP82 integrated were mated to haploids that had: 1) hsc82$\Delta$ and pRS305-pUG72 for strain Lo90; 2) hsc82$\Delta$ and pRS305-pUG72-HSC82 in for strain Re90; or 3) hsc82$\Delta$ and pRS305-pUG72-HSC82out for strain Hi90. Diploids were picked and grown overnight in YPD prior to sporulation in liquid medium (1). After 4-6 days at 23° C., tetrads were dissected (Singer Instruments MSM System) to obtain haploids of both mating types that harbored hsc82$\Delta$, hsp82$\Delta$, pRS303-LEP-HSP82 and either pRS305-pUG72 (strain Lo90), pRS305-pUG72-HSC82 in (strain Re90), or pRS305-pUG72out (strain Hi90). These strains were back crossed for three rounds to the parental W303 strains to minimize any spurious mutations due to transformation. The back-crossed strains were transformed with plasmid pSH63 containing cre recombinase under the control of the GAL1 promoter (3). The transformation protocol used for these strains employed reduced temperatures compared to the standard protocol, with the 42° C. heat shock treatment replaced by two hours incubation at 30° C. Transformants were verified to have the cre plasmids with primers CRE-F and CRE-R.

*Candida Albicans* Strains

Figure 5:
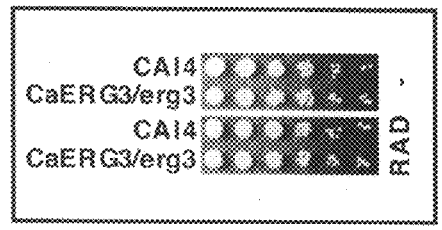
FIG. 5. The importance of Hsp90 in FL resistance in *C. albicans*. (A) Hsp90 inhibition blocked the emergence of FL resistance in a laboratory strain wild-type for ERG3 (CAI4) and in a heterozygous ERG3 mutant. Selection with 128 µg/ml FL alone (left panels) or with FL plus 1 µM RAD (right panels). (B) FL resistance of clinical isolates was initially Hsp90 dependent but evolved towards Hsp90 independence. FL sensitivity of CAI4 and FL resistance of serial clinical specimens of the same strain (CaCi) isolated from an HIV patient receiving fluconazole over a two year period (left panel); isolates from the in vivo selection are ordered sequentially, with those recovered early at the top. Middle and right panels, inhibition of Hsp90 by GdA (5 µM) or calcineurin by CsA (20 µM) in rich medium with FL. Data analyzed as in FIG. 1. (C) Elevated temperatures reduce FL resistance of CaCi isolates (shown in the same order as in part B) in synthetic medium, RPMI.

Archives of all *C. albicans* strains were maintained in 25% glycerol at $-80°$ C. The heterozygous ERG3 deletion mutant (CaERG3/erg3) was constructed in the CAI4 background using a recyclable URA3-dpl200 cassette with 200 bp flanking repeats (8). The URA3 disruption cassette was amplified from plasmid pDDB57 with primers CaERG3-5'KO and CaERG3-3'KO and strains were transformed according to a standard protocol (8). Deletion of ERG3 was verified with two sets of primers: 1) CaERG3-5' detect and CaURA3-R; and 2) CaERG3-3' detect and CaURA3-F. Subsequently, cells that lost URA3 due to recombination between the flanking repeats were selected on 5-fluoroorotic acid (5-FOA, BioVectra Diagnostic Chemicals, Ltd.) plates (1). Excision of URA3 was confirmed based on the size of the PCR product obtained with primers CaERG3-5' detect and CaERG3-3' detect (a 1.8 kb product was obtained for wild-type strains, a 2.2 kb product for strains with the integrated URA3 cassette, and a 1 kb product for strains that subsequently lost the URA3 cassette). Strains were also verified by Southern blot analysis. For growth of CAI4 and CaERG3/erg3 in the two synthetic defined media employed in this study, SD (1) and RPMI (9), uridine was supplemented at 80 µg/ml (Sigma-Aldrich Co.). Specimens from a series of 17 clinical isolates that evolved resistance in a HIV-infected patient over the course of two years of fluconazole treatment were generously provided by Theodore White (10-12) and were originally collected by Spencer Redding and colleagues. The isolates shown in FIG. 5 are: #2-9, 11, 12, and 15-17. Clinical isolate T118 was also from an HIV-infected patient and was characterized as sensitive to fluconazole in synthetic defined media in previous studies (13, 14).

Induction of Cre Recombinase to Excise loxP-Flanked Cassettes

Strains were grown at 23° C. to mid-logarithmic growth phase in synthetic defined SD medium lacking histidine (HIS), leucine (LEU), tryptophan (TRP) and uracil (URA) to maintain selection for the integrated and centromeric plasmids (amino acid supplements from Qbiogene, Inc.). Cells were washed with water and transferred to SGal medium (as SD, but with 2% galactose instead of glucose) lacking HIS, LEU and TRP to induce the expression of cre recombinase from the GAL1 promoter and to enable excision of the loxP-flanked URA3 cassettes. After six hours, dilutions were plated on SD lacking HIS, LEU, and TRP. After several days, colonies were replica plated onto two sets of plates: 1) SD plates lacking HIS, LEU, TRP, and URA (to identify cells that still had the cassette present); and 2) 5-FOA plates lacking HIS, LEU, and TRP (to identify the cells in which the loxP-flanked URA3 cassette was excised). Excision of the cassette was confirmed by PCR with primers HSC82-6F and KL-URA3-R. Western blot analysis was employed to confirm that strains had the expected levels of Hsp90 expression before and after cre-mediated recombination.

DNA Sequencing

For sequencing, plasmid DNA was prepared using Qiagen Miniprep Kits (Qiagen) and PCR products were purified using Qiagen PCR Purification Kits. Samples were sent for sequencing with the indicated primers (table S2) to Northwoods DNA, Inc. Plasmids containing HSC82 were sequenced with primers HSC82-5R, HSC82-2F, HSC82-3F, HSC82-4F, HSC82-5F, and HSC82-6F. Plasmids containing HSP82 were sequenced with primers HSP82-1F, O-273, O-193, HSP82-2F, HSP82-3F, HSP82-4F, O-274, and O-276. ERG3 was amplified from genomic DNA of S. cerevisiae strains with primers ERG3-F1 and ERG3-R1. Independent PCR amplified products from each strain were combined, purified, and sequenced with primers ERG3-F1-4. The complementary strand was sequenced with primers ERG3-R1, ERG3-R4 and ERG3-R5. PDR1 was amplified from S. cerevisiae strains with primers PDR1-F1 and PDR1-R1. Independent PCR amplified products from each strain were combined, purified, and sequenced with PDR1-R1. ERG3 was amplified from genomic DNA of C. albicans strains with primers CaERG3-F1 and CaERG3-R1. Independent PCR reactions were pooled for each sample, purified, and sequenced with primers CaERG3-F1-4 and CaERG3-R1-4.

Antifungal Susceptibility Testing

Resistance to fluconazole (FL, Pfizer, Inc. and Sequoia Research Products Ltd.) was determined in flat bottom, 96-well microtiter plates (VWR) using a broth microdilution protocol modified from the NCCLS M27-A standard (9). These minimum inhibitory concentrations (MIC) tests were set up in a total volume of 0.2 ml/well with FL concentrations of 0, 16, 32, 64, 128, and 256 µg/ml as described in Anderson et al. (4). Cell densities of overnight cultures were determined and dilutions were prepared such that ~$10^3$ cells were inoculated into each well. Radicicol (RAD, A.G. Scientific, Inc.) and geldanamycin (GdA, Alexis Biochemicals) were employed to inhibit Hsp90 at the concentrations indicated in the figure legends (1-5 µM). Cyclosporin A (CsA, CalBiochem) was employed to inhibit calcineurin at a concentration of 20 µM. Dimethyl sulfoxide (DMSO, Sigma-Aldrich Co.) was the solvent for RAD, GdA, and CsA. Thus, the maximum final DMSO concentration (0.14%) was included in FL MIC tests performed in the absence of RAD, GdA, or CsA to control for any solvent effects.

Plates were incubated in the dark at temperatures ranging from 23° C. to 39° C., as indicated in the figure legends. After 48 hours, plates were sealed with a clear film (Axygen Scientific), re-suspended by agitation, and absorbance was determined at 595 nm with the Multiskan Ascent photometer (Thermo Labsystems, Thermo Electron Corporation). Absorbance values were corrected for background from the corresponding medium. MICs were determined as the concentration of FL that inhibits fungal growth by 50% relative to the FL-free growth control. The MIC of each strain was tested at least two independent times in duplicate. Most strains were tested in rich medium (half-strength YPD) and SD medium. C. albicans clinical isolates were also tested in the synthetic defined medium that is the standard for clinical testing, RPMI (9). For FIGS. 1, 3, 5, S2, and S4, MIC data was quantitatively displayed with color using the program TreeView 1.0.10 (http://genetics.stanford.edu/~alok/TreeView/).

Resistance of C. albicans clinical isolate T118 and A. terreus soil isolate ATCC 10020 to FL, voriconazole (VO), and caspofungin (CS) was determined with Etest strips (AB Biodisk) on rich medium (half-strength YPD). For C. albicans, standardized inoculum was prepared as described above and ~$10^5$ cells were plated on medium with the Hsp90 inhibitor RAD (5 µM), the calcineurin inhibitor CsA (20 µM), or the solvent control (0.14% DMSO), prior to application of a test strip. Plates were photographed after 36 hours at 30° C. in the dark. For A. terreus, inoculum was prepared according to a standard protocol (15) and ~$10^5$ conidia were plated prior to application of a test strip. Plates were photographed after 36 hours at 35° C. in the dark.

Selection of Fluconazole-Resistant Mutants in S. Cerevisiae

For selection of FL resistance in S. cerevisiae by a rapid, one-step regime, Lo90, Re90, and Hi90 strains were grown in SD medium lacking HIS, LEU, TRP and URA at 23° C. until stationary phase. Cell counts were performed with a hemacytometer and dilutions were plated onto SD medium lacking HIS, LEU, TRP and URA to estimate the number of viable colony forming units. ~$10^4$ cells were plated on three SD plates of the same composition but supplemented with 128 µg/ml FL. The selection experiment was repeated on three separate occasions and all selection plates were photographed under standard conditions after seven days at 23° C.

Images were analyzed with CellProfiler (www.cellprofiler.org) by the following steps: (1) the red channel was extracted from the color images; (2) the gradients in illumination across each plate were corrected by calculating the minimum intensities in 20×20 pixel neighborhoods across the image, smoothing these minimums by taking the median within disk-shaped neighborhoods of radius 20 pixels, and dividing the image by the resulting smoothed illumination function; (3) images were cropped to standard dimensions and to remove the plate rim and the region with lighting artifacts due to glare; (4) colonies were identified with an algorithm for detecting local maxima in the distance transform of the image using an automatically determined threshold and a maxima suppression neighborhood of three; (5) dividing lines between clumped colonies were identified using a watershed on the distance transformed image; (6) the area of the identified colonies was measured; (7) colonies were classified as small ($\leq 0.67$ mm$^2$), intermediate, or large ($\geq 1.59$ mm$^2$); (8) images were processed to color code colonies by size.

The threshold for the smallest size class was set to distinguish the small abortive colonies from colonies that grew upon subculturing on plates with 128 µg/ml FL. The threshold for the large colonies was set to identify colonies with true increases in resistance among those that grew upon subculturing on plates with FL. After subculturing on plates with FL, twenty-four colonies of the intermediate and of the large size classes were tested for FL MICs. True resistance was defined by an increase in MIC relative to the parental strain.

For selection of resistance by a regime that favors mutations in PDR1 (16), triplicate populations of Lo90, Re90, and Hi90 strains were grown to saturation in SD medium lacking HIS, LEU, TRP, and URA at 23° C. Then, ~5×10$^4$ cells were inoculated into 50 ml of the same medium with 16 μg/ml FL and growth was monitored spectrophotometrically over 6 days at 23° C. When cultures reached high densities of ~10$^7$ cells/ml (day 5 or 6), they were plated for single colonies.

Selection of Fluconazole-Resistant Mutants in C. Albicans

Strains of C. albicans were grown at 30° C. in SD prior to plating ~10$^4$ cells on SD plates with 128 μg/ml FL or with both 128 μg/ml FL and 1 μM RAD. Plates were photographed after 7 days at 30° C. in the dark.

Serial Cell Dilution Assays

Strains were grown to saturation in SD medium and cell concentrations were standardized based on optical density. Five-fold dilutions, starting from ~4×10$^6$ cells/ml, were spotted on media, as indicated in the figure legends, using a spotter (Frogger, V&P Scientific, Inc). The plates were photographed after 2-3 days in the dark at the indicated temperature. For all spotting assays in which Hsp90 or calcineurin inhibitors were employed, the corresponding plates without these inhibitors was supplemented with the maximum final concentration of DMSO used (0.14%), as a solvent control.

Western Blot Analysis

Yeast cells were grown in SD medium to mid-log phase and protein was extracted following a standard protocol (17). Protein concentrations were determined both by Bradford assay (17) and by optical density at 280 nm (Nanodrop Technologies). Total cellular protein (~10 μg) was separated by electrophoresis (Criterion 4-15% Precast Gels, Biorad) and transferred to PVDF membrane (Immobilon P, Millipore). Blots were hybridized with an antibody against Hsp90 (1:5000, (18)) or Pdr5 (1:10,000, (19)) as well as an antibody against tubulin as a loading control (1:1000, Abcam Ltd.).

Supporting Tables

TABLE S1

Strains of S. cerevisiae used in this study

| Strain[a] | Relevant Genotype | Reference or Source |
|---|---|---|
| S288C-1 (P3) | MATa ura3::KAN | (4) |
| S288C-2 (P4) | MATa ura3::KAN | (4) |
| G1 (D2-400) | MATa ura3::KAN Pdr1 T817K | (4) |
| G2 (D3-400) | MATa ura3::KAN Pdr1 C862W | (4) |
| G3 (D4-400) | MATa ura3::KAN Pdr1 L722P | (4) |
| R1 (O1) | MATa ura3::KAN Erg3 T148stop | (4) |
| R2 (O2) | MATa ura3::KAN Erg3 T267P | (4) |
| R3 (O3) | MATa ura3::KAN Erg3 I270T | (4) |
| BY4741 | MATa his3Δ leu2Δ met15Δ ura3Δ | (5, 6) |
| erg3Δ | As By4741, erg3::KAN | (Yeast deletion library) |
| erg6Δ | As By4741, erg6::KAN | (Yeast deletion library) |
| ymr102cΔ | As By4741, ymr102c::KAN | (Yeast deletion library) |
| ymr099cΔ | As By4741, ymr099c::KAN | (Yeast deletion library) |
| ypl056cΔ | As By4741, ypl056c::KAN | (Yeast deletion library) |
| osh1Δ | As By4741, osh1::KAN | (Yeast deletion library) |
| scs2Δ | As By4741, scs2::KAN | (Yeast deletion library) |
| cka2Δ | As By4741, cka2::KAN | (Yeast deletion library) |
| ybr147wΔ | As By4741, ybr147w::KAN | (Yeast deletion library) |
| ygr283cΔ | As By4741, ygr283c::KAN | (Yeast deletion library) |
| ylr407wΔ | As By4741, ylr407w::KAN | (Yeast deletion library) |
| W303a | MATa ade2-1 can1-100 his3-12,16 leu2-3,112 trp1-1 ura3-1 | (18) |
| W303α | As W303a, but MATα | (18) |
| Lo90-NL-a | As W303a, hsc82::KAN hsp82::KAN LEP-HSP82-HIS3 | This Study |
| Lo90-NL-α | As Lo90-NL-a, but MATα | This Study |
| Lo90-a | As Lo90-NL-a, loxURA3lox-LEU2 | This Study |
| Lo90-α | As Lo90-a, but MATα | This Study |
| Re90-a | As Lo90-NL-a, loxHSC82URA3lox-LEU2 | This Study |
| Re90-α | As Re90-a, but MATα | This Study |
| Hi90-a | As Lo90-NL-a, HSC82loxURA3lox-LEU2 | This Study |
| Hi90-α | As Hi90-a, but MATα | This Study |
| Re90-FLR-1a | As Re90a, ERG3 A496T (K->stop) | This Study |
| Re90-FLR-2a | As Re90a, ERG3 296-298 TTG del | This Study |
| Re90-FLR-3a | As Re90a, ERG3 284-285 CA del | This Study |
| Re90-FLR-1α | As Re90α, ERG3 C425A (A->E) | This Study |
| Re90-FLR-2α | As Re90α, ERG3 869 T del | This Study |
| Re90-FLR-3α | As Re90α, ERG3 A273T (R->S) | This Study |
| Hi90-FLR-1a | As Hi90a, ERG3 914-915 TG del | This Study |
| Hi90-FLR-2a | As Hi90a, ERG3 T612A (H->Q) | This Study |
| Hi90-FLR-3a | As Hi90a, ERG3 T673A (F->I) | This Study |
| Hi90-FLR-1α | As Hi90α, ERG3 G272T (R->I) | This Study |
| Hi90-FLR-2α | As Hi90α, ERG3 C245A (S->stop) | This Study |
| Hi90-FLR-3α | As Hi90α, ERG3 270-271 GA del | This Study |

[a]Strain name used in referenced study is provided in parentheses.

TABLE S2

Primers Used in This Study

| Name | Sequence 5' to 3' |
|---|---|
| HSC82-KANMX4-F | GAACAGATTGACAAGCTTTTAACCGTACTAGATAGTTTATAACCCCTATAGGGAGACCGGCAGATCC |
| HSC82-KANMX4-R | AGATCAATGAAATTTATTGAACAAAGTTGCAAAGGTGAGTAAATAACAGCTGAAGCTTCGTACGC |
| HSP82-KANMX4-F | ATAGAGTCCTATAAACAAAAGCACAAACAAACACGCAAAGATATGCTCGTTTTCGACACTGGATGG |
| HSP82-KANMX4-R | TTATGTTTTGTTTATAACCTATTCAAGGCCATGATGTTCTACCTACTGTTTAGCTTGCCTCGTCC |
| HSP82-SpeI-F | GCCAACTAGTTCTTAACATCTGTGACCTCCTC |
| HSP82-BamHI-R | ACGCGGATCCTTTCACGATTTCAGATTCTTCG |
| HSC82-SacI-F | GGCAGAGCTCCCCATTACGCATTTGATTATAATTTGC |
| HSC82-NcoIB-R | GCCACCATGGGTCATTCGTAAGTGTACACTAAAC |
| HSC82-SacII-F | GGCACCGCGGCCCATTACGCATTTGATTATAATTTGC |
| HSC82-SpeIB-R | GCCAACTAGTGTCATTCGTAAGTGTACACTAAAC |
| CRE-F | GCTTCAAAAATCCCTTCCAGG |
| CRE-R | ACCGTACACCAAAATTTGCC |
| ERG3-F1 | CGCGGTATATATTAGAGGCG |
| ERG3-F2 | CTTTGAACTCCAAGAATGCC |
| ERG3-F3 | GTGTAAGGAAGCTCATTATCG |
| ERG3-F4 | CCTATCAAACAATCCTGCC |
| ERG3-R1 | GCATATTGCACTAACGTGAGG |
| ERG3-R4 | GCAGGATTGTTTGATAGG |

TABLE S2-continued

Primers Used in This Study

| Name | Sequence 5' to 3' |
|---|---|
| ERG3-R5 | CAACATCGACATCCATGG |
| HIS3-R | GAAGAAACCACCGTTGCC |
| HSC82-2F | ATGGCTGGTGAAACTTTTG |
| HSC82-3F | TGGTAGAGGTACCGTCTTGAG |
| HSC82-4F | GTTGTACGTTCGTCGTGTC |
| HSC82-5F | CGAATTGGAAGAAACAGACG |
| HSC82-5R | CAGCAGATAGAGCTTCCATG |
| HSC82-6F | TCCAGCTGACACCGAGATG |
| HSP82-1F | CTTCCCGCTGTATTAGAGTTC |
| HSP82-1R | CAGTTATTTCCATGCAGATGC |
| HSP82-2F | CCATGATTGGTCAATTCGG |
| HSP82-3F | ACAAGACTAAGCCTTTGTGG |
| HSP82-4F | GAAGCCTTCAACGAAATTGC |
| KANMX4-F | CAATTCAACGCGTCTGTGAG |
| KANMX4-R | CTCCTTCATTACAGAAACGGC |
| KL-URA3-F | CCCAGGTGTAGGTTTAGACG |
| KL-URA3-R | TGCAGACCGATCTTCTACC |
| LEU2-Down | CGTTATCCAGGGTGTGTTAACG |
| LEU2-2R | CAGATTCCCTTTTATGGATTCC |
| O-273 | AGGCCTTGGTCAATGGTTCA |
| O-193 | CTTTTCTTCTTCTGGAATTGGAAC |
| O-274 | GGTTTTGTTCTTGACCGACC |
| O-276 | TTCGTTGAAGGCTTCAATCA |
| PDR1-F1 | GAATCTGATAATATTGTCGCC |
| PDR1-R1 | TCATTTGACATTAGTGGTTCC |
| YMR185W-F | CGTGATCAAGATGAAGATTACATGG |
| YMR187C-R | GGTCAAGTCTGAAGCTCTATGCC |
| 3-PRS30X | GGTTACGCGCAGCGTGAC |
| 5-pRS30X | GGTTATTGTCTCATGAGCGG |
| CaERG3-5'KO | TAGATATCTTTGGACATTCTATTCCCTTC CCATTTCTTTCCCTATTGTGCATATAAGTT CTTTCCCAGTCACGACGTTG |
| CaERG3-3'KO | AGAAAACTCTCAAGATTGTCCTTAATCTT CATCAATATCATCATCACGACCGGGACC TTATGTGGAATTGTGAGCGGATA |
| CaERG3-5'detect | CAACTAAGGTCAACCTTCCC |
| CaURA3-R | GAGTTTCTGCTCTCTCAC |
| CaERG3-3'detect | CATCACACACGTGCCACAC |
| CaURA3-F | GAAATGCTGGTTGGAATGC |
| CaERG3-F1 | CATTTCTTTCCCTATTGTG |
| CaERG3-F2 | GCTCCTAAATTTTTCCCAGC |
| CaERG3-F3 | CATAGATGGTTACACTGGC |
| CaERG3-F4 | CAGTTGTCAATGGTACCG |
| CaERG3-R1 | GGAAAAATAGTCAATGGTCC |
| CaERG3-R2 | GGTACCATTGACAACTGG |
| CaERG3-R3 | GCCAGTGTAACCATCTATG |
| CaERG3-R4 | GCTGGGAAAAATTTAGGAGC |

SUPPORTING REFERENCES

1. F. M. Ausubel et al., *Current Protocols in Molecular Biology* (John Wiley & Sons, New York, 1987).
2. H. C. Chang, S. Lindquist, *J. Biol. Chem.* 269, 24983 (1994).
3. U. Gueldener, J. Heinisch, G. J. Koehler, D. Voss, J. H. Hegemann, *Nucleic Acids Res.* 30, e23 (2002).
4. J. B. Anderson et al., *Genetics* 163, 1287 (2003).
5. E. A. Winzeler et al., *Science* 285, 901 (1999).
6. G. Giaever et al., *Nature* 418, 387 (2002).
7. A. Wach, A. Brachat, R. Pohlmann, P. Philippsen, *Yeast* 10, 1793 (1994).
8. R. B. Wilson, D. Davis, B. M. Enloe, A. P. Mitchell, *Yeast* 16, 65 (2000).
9. NCCLS, *Reference method for broth dilution antifungal susceptibility testing of yeasts. Approved standard M27-A.* (NCCLS, Wayne, Pa., 1997).
10. T. C. White, *Antimicrob. Agents Chemother.* 41, 1488 (1997).
11. T. C. White, *Antimicrob. Agents Chemother.* 41, 1482 (1997).
12. T. C. White, M. A. Pfaller, M. G. Rinaldi, J. Smith, S. W. Redding, *Oral Dis.* 3 Suppl 1, S102 (1997).
13. L. E. Cowen et al., *Antimicrob. Agents Chemother.* 43, 2930 (1999).
14. L. E. Cowen et al., *J. Bacteria* 182, 1515 (2000).
15. NCCLS, *Reference method for broth dilution antifungal susceptibility testing of filamentous fungi. Approved standard M38-A.* (NCCLS, Wayne, Pa., 2002).
16. J. B. Anderson, C. Sirjusingh, N. Ricker, *Genetics* 168, 1915 (2004).
17. N. Johnsson, A. Varshaysky, *EMBO J.* 13, 2686 (1994).
18. K. A. Borkovich, F. W. Farrelly, D. B. Finkelstein, J. Taulien, S. Lindquist, *Mol. Cell. Biol.* 9, 3919 (1989).
19. R. Egner, Y. Mahe, R. Pandjaitan, K. Kuchler, *Mol. Cell. Biol.* 15, 5879 (1995).

What is claimed is:

1. A method of overcoming antifungal drug resistance in an individual infected by a fungus comprising coadministering to the individual at least one antifungal drug to which the fungus has developed resistance and at least one Hsp inhibitor that reduces cytoplasmic Hsp90 function in the fungus, wherein the at least one antifungal drug is an azole or echinocandin.

2. The method of claim 1, wherein the individual in need thereof has a *Candida* infection or an *Aspergillus* infection and the Hsp inhibitor is an Hsp90 inhibitor.

3. The method of claim 1, wherein the at least one Hsp90 inhibitor is (a) geldanamycin, 17-allylamino-17-demethoxygeldanamycin (17-AAG), or 17-(desmethoxy)-17-dimethylaminoethylamino-geldanamycin (17-DMAG) or (b) radicicol.

4. The method of claim 2, wherein the individual in need thereof has an *Aspergillus fumigatus* infection and the at least one antifungal drug is caspofungin.

5. A method of enhancing the therapeutic effectiveness of an antifungal drug in an individual that has an infection by a drug resistant fungus, comprising coadministering to the individual at least one antifungal drug and at least one Hsp90 inhibitor that reduces cytoplasmic Hsp90 function in the fungus, wherein the at least one antifungal drug is an azole or echinocandin to which the fungus has developed resistance.

6. The method of claim 5, wherein the drug resistant fungal infection is a drug resistant yeast infection.

7. The method of claim 6, wherein the drug resistant yeast infection is a drug resistant *Candida* infection or a drug resistant *Aspergillus* infection.

8. The method of claim 7, wherein the at least one antifungal drug is an azole or an echinocandin.

9. The method of claim 8, wherein the at least one Hsp90 inhibitor is (a) geldanamycin, 17-allylamino-17-demethoxygeldanamycin (17-AAG), or 17-(desmethoxy)-17-dimethylaminoethylamino-geldanamycin (17-DMAG) or (b) radicicol.

10. The method of claim 8, wherein the individual in need thereof has an *Aspergillus fumigatus* infection and the at least one antifungal drug is caspofungin.

11. A method of inhibiting the development of antifungal drug resistance in an individual in need thereof, comprising coadministering to the individual at least one antifungal drug and at least one Hsp90 inhibitor that reduces cytoplasmic Hsp90 function in a fungus and inhibits emergence of mutant strains of said fungus that are resistant to said antifungal drug, wherein the Hsp90 inhibitor renders fungal cells, having one or more mutations that would, in the absence of the Hsp90 inhibitor, confer resistance to said antifungal drug, sensitive to the antifungal drug, so that development of antifungal drug resistance is inhibited, wherein the at least one antifungal drug is an azole or an echinocandin.

12. The method of claim 11, wherein the individual in need thereof has a *Candida* infection or an *Aspergillus* infection.

13. The method of claim 11, wherein the at least one Hsp90 inhibitor is (a) geldanamycin, 17-allylamino-17-demethoxygeldanamycin (17-AAG), or 17-(desmethoxy)-17-dimethylaminoethylamino-geldanamycin (17-DMAG) or (b) radicicol.

14. The method of claim 11, wherein the individual in need thereof has an *Aspergillus fumigatus* infection and the at least one antifungal drug is caspofungin.

15. A method of reducing antifungal drug resistance of a fungus comprising exposing the fungus to at least one antifungal drug and at least one inhibitor that reduces Hsp90 function in the fungus, wherein the at least one antifungal drug is an azole or echinocandin, and wherein the Hsp90 inhibitor impairs the fungal stress response and reduces resistance to said antifungal drug of fungal cells having one or more loss of function mutations that would otherwise confer resistance to said antifungal drug.

16. The method of claim 15, wherein the fungus is *Candida*.

17. The method of claim 15, wherein the fungus is *Candida* or *Aspergillus*.

18. The method of claim 15, wherein the fungus is a yeast.

19. The method of claim 15, wherein the fungus is *Candida* or *Aspergillus* and the at least one antifungal drug is an azole or an echinocandin.

20. The method of claim 1, wherein the at least one antifungal drug is an azole, and wherein the Hsp inhibitor overcomes resistance of the fungus to the azole.

21. The method of claim 5, wherein the at least one antifungal drug is an azole, and wherein the Hsp90 inhibitor reduces resistance of the fungus to the azole.

22. The method of claim 11, wherein the at least one antifungal drug is an azole.

23. The method of claim 15, wherein the at least one antifungal drug is an azole, and wherein the Hsp90 inhibitor reduces resistance of the fungus to the azole.

24. The method of claim 1, wherein the antifungal drug is an azole or echinocandin, and the Hsp inhibitor is capable of overcoming antifungal drug resistance to said drug acquired through diverse mutations.

25. The method of claim 5, wherein the Hsp90 inhibitor is capable of reducing antifungal drug resistance to said antifungal drug acquired through diverse mutations.

26. The method of claim 11, wherein the Hsp90 inhibitor is capable of reducing antifungal drug resistance to said antifungal drug acquired through diverse mutations.

27. The method of claim 15, wherein the Hsp90 inhibitor is capable of reducing antifungal drug resistance to said antifungal drug acquired through diverse mutations.

* * * * *

UNITED STATES PATENT AND TRADEMARK OFFICE
CERTIFICATE OF CORRECTION

| | |
|---|---|
| PATENT NO. | : 8,343,913 B1 |
| APPLICATION NO. | : 11/175515 |
| DATED | : January 1, 2013 |
| INVENTOR(S) | : Cowen et al. |

It is certified that error appears in the above-identified patent and that said Letters Patent is hereby corrected as shown below:

In the claims:

Column 20, line 28, Claim 3, the first line, change "1" to --2--.

Signed and Sealed this
Thirteenth Day of August, 2013

Teresa Stanek Rea
*Acting Director of the United States Patent and Trademark Office*